United States Patent [19]

Hubred

[11] Patent Number: 5,162,214
[45] Date of Patent: Nov. 10, 1992

[54] CMA PRODUCTION UTILIZING ACETATE ION EXCHANGE FROM FERMENTATION BROTH

[75] Inventor: Gale L. Hubred, Richmond, Calif.

[73] Assignee: General Atomics International Services Corporation, San Diego, Calif.

[21] Appl. No.: 681,143

[22] Filed: Apr. 5, 1991

[51] Int. Cl.⁵ .................... C12P 7/40; C12P 7/54; C07C 51/42; C09K 3/18

[52] U.S. Cl. .................... 435/136; 252/70; 435/140; 435/168; 435/280; 435/803; 435/813; 562/606; 562/607; 562/608

[58] Field of Search ............... 435/168, 136, 140, 803, 435/813, 280; 252/70; 562/606, 607, 608

[56] References Cited

U.S. PATENT DOCUMENTS

| | | | |
|---|---|---|---|
| Re. 32,609 | 2/1988 | Gancy | 562/607 |
| 3,944,606 | 3/1976 | Rieger et al. | 562/584 |
| 4,275,234 | 6/1981 | Baniel et al. | 562/584 |
| 4,377,488 | 3/1983 | Gancy | 562/608 |
| 4,430,242 | 2/1984 | Gancy | 252/70 |
| 4,444,881 | 4/1984 | Urbas | 562/606 |
| 4,636,467 | 1/1987 | Chynoweth | 435/140 |
| 4,673,519 | 6/1987 | Gancy | 252/70 |
| 4,913,831 | 4/1990 | Todd et al. | 562/608 |

OTHER PUBLICATIONS

*Englewood* (North Dakota) *Monthly*, Mar. 1991.

*Primary Examiner*—Herbert J. Lilling
*Attorney, Agent, or Firm*—Heller, Ehrman White & McAuliffe

[57] ABSTRACT

A method is provided for removing an anion from an aqueous liquid, such as a fermentation broth. The aqueous broth is contacted with a water-immiscible ion exchange liquid to extract the anion from the broth. The anion exchange liquid is then back extracted with an aqueous phase, to remove the anion, preferably for other uses.

9 Claims, 1 Drawing Sheet

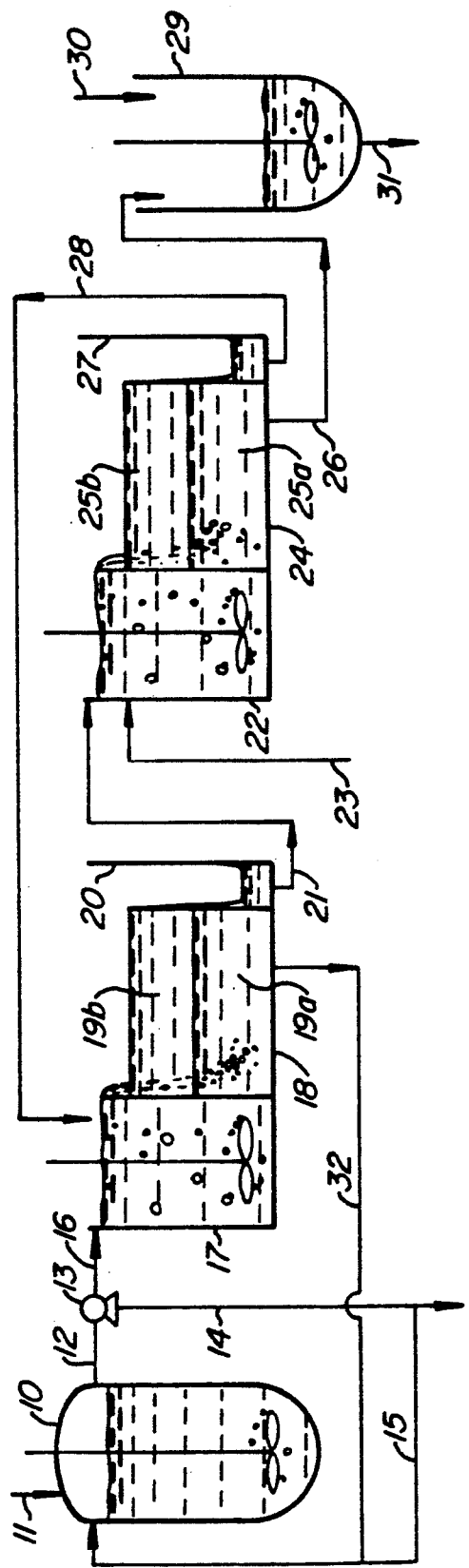
FIGURE

CMA PRODUCTION UTILIZING ACETATE ION EXCHANGE FROM FERMENTATION BROTH

The present invention is directed to a method for removing anion from an aqueous liquid, such as a fermentation broth, which can be performed in a continuous manner.

The method is particularly useful for exchanging acetate ion from an acetate-producing fermentation broth for hydroxyl ion and directing the extracted acetate ion to a reaction vessel where the acetate may be used in an acetate-consuming chemical process while disposing of the hydroxyl ion by a neutralizing reaction to form water. The method is particularly useful for extracting acetate ion from an acetate-producing fermentation broth and using the extracted acetate to making calcium-magnesium acetate (CMA).

BACKGROUND OF THE INVENTION

According to the present invention an anion is recovered from an aqueous liquid, such as acetate from an acetate-producing fermentation broth, by extraction with an ion exchange non-aqueous liquid. The present invention is particularly advantageous for extracting anions from fermentation broths since fermentation which produces, for example, acetic acid, is limited because the accumulated level of acetic acid inhibits further biological production.

Many fermentation processes also result in decrease in production of the desired anion when pH change due to fermentation is sufficient to inhibit the organisms.

One method which may be utilized to remove the anion (such as acetate) is to extract it from the fermentation broth using an extraction solvent which takes advantage of solubility partition coefficients. This, however, has inherent inefficiencies since the anion must be first converted to a species soluble in the non-aqueous extraction liquid, which is usually accomplished by altering the pH of the fermentation product.

Other methods involve removal of the fermentation product, such as citric acid, by a membrane separator, which can be slow and involves specialized membrane technology.

If the fermentation product such as acetate, is to be used as a feed for a chemical process, another way of removing the anion is to add the other reactants of the chemical process directly to the fermentation broth. For example, dolomitic lime might be added directly to a fermentation broth containing acetic acid to make CMA. This, however contaminates the fermentation broth. Therefore, by direct addition of lime to the broth either the culture cannot be used in a continuous manner or the fermentation broth must be continuously replenished.

However, it is not believed that a method has been heretofore known for removing anions from an aqueous liquid, such as a fermentation broth, in a continuous manner by using an ion exchange liquid for extraction, whereby the anion is extracted from the fermentation liquid in a continuous manner, then back-extracted from the ion-exchange liquid and used directly as a starting material for a chemical process. The present invention provides such a method and, additionally, has the advantageous features of neutralizing the acid produced in the broth with hydroxyl ion to produce water. Furthermore, by back-extraction, direct contact of the chemical reactants (lime) with the broth is avoided, thereby minimizing undesirable perturbations of the extraction process from the broth.

SUMMARY OF THE INVENTION

The present invention provides a method for removing an anion from an aqueous liquid comprising the steps of contacting the aqueous anion-containing liquid with a non-aqueous extraction liquid comprising an anion exchange reagent which exchanges a back extraction anion with the anion in the aqueous liquid to thereby extract the anion from the aqueous liquid; separating the extraction liquid containing the extracted anion from the aqueous liquid; contacting the extraction liquid containing the extracted anion with a second aqueous phase preferably comprising reactants which react with the anion to form a water-soluble product dissolved in the second aqueous phase; separating the second aqueous phase containing the dissolved product from the extraction liquid; optionally isolating the product from the second aqueous phase. The method is particularly useful when the anion-containing liquid is a fermentation broth which produces the anion and the second aqueous phase comprises calcium and magnesium hydroxide which exchange with the acetate for hydroxide to form water-soluble calcium-magnesium acetate, which also neutralizes acid to form water.

DESCRIPTION OF THE DRAWINGS

FIG. 1 is a schematic view of a preferred apparatus used to perform the present invention.

DESCRIPTION OF THE PREFERRED EMBODIMENTS

The present invention is useful for removing an anion, such as a fermentation product, from an aqueous liquid by extraction using an ion exchange reagent. The extraction liquid containing the ion exchange reagent is then back extracted with a second aqueous phase which may contain reactants which react with the anion and which donate a back extraction anion to the extraction liquid. Therefore, by recycling the extraction liquid, there is a net flow of back-extraction anion back into the aqueous liquid, which back-extraction anion is preferably a base, thereby providing a means for controlling the pH of the aqueous liquid.

The preferred ion exchange liquids are quaternary ammonium compounds, such as those known in the ALIQUAT® series. made by Henkel. The back-extracting anion is preferably hydroxide ion, provided preferably from calcium and magnesium hydroxides. The invention will be described in connection with FIG. 1 which shows the preferred embodiment of the present invention. Referring to FIG. 1, the fermentor 10 containing a fermentation broth is maintained under fermentation conditions to produce the product, preferably acetate. Acetate-producing microorganisms and conditions for their fermentation are known in the art. The culture nutrients may be fed into the fermentor 10 through line 11. Broth is then removed through line 11 and the cells are separated by separator 13, such as a centrifuge, and directed through line 14 from which they can be disposed or recycled through line 15 into fermentor 10. The clarified broth is conducted via line 16 into extractor 17 containing the non-aqueous extraction ion exchange liquid. The clarified aqueous broth and the non-aqueous extraction liquid are mixed in the extractor 17 by stirring and as extractor 17 is filled the overflow spills into separation tank 18 where the contents are allowed to separate into two phases 19A and 19B. As shown, 19B is the non-aqueous phase comprising the ion exchange liquid and the anion which has now been extracted from the aqueous phase 19A. The non-aqueous phase spills into collector 20 from which it is drained via line 21 and directed into the back extractor 22. The aqueous slurry containing calcium and magnesium hydroxide (preferably in the form of dolime) is introduced into the back extractor 22 via line 23. The contents of the back extractor 22 are stirred whereby the calcium and magnesium ions react with the acetate ion to form water-soluble calcium-magnesium acetate. The overflow from tank 22 is spilled into settling tank 24 in which the liquids are allowed to settle into two phases 25A and 25B. As shown, the lower aqueous phase 25A contains the dissolved desired product calcium-magnesium acetate which can be withdrawn via line 26. The organic phase containing the ion exchange liquid 25B, now having a hydroxide counter-ion, is spilled into collecting tank 27 and recycled via line 28 into the extractor 17. The calcium-magnesium acetate-containing slurry may be then directed into a processing tank 29 in which the pH may be adjusted by adding acetic acid via line 30. The calcium-magnesium acetate slurry at the desired pH is then withdrawn through line 31. The broth from tank 18 may be recycled into the fermentor 10 via line 32.

To make CMA, preferably the clarified fermentation broth entering tank 17 through line 16 will be at a pH around 6. The aqueous broth recycle phase 19A will be at a pH of about 6.5 and the CMA slurry 25A in tank 24 will be at a pH of about 8. In the processing tank 29 the CMA may be adjusted preferably to a pH of about 7.

Other modifications will be readily perceived from the above description to include, but not limited to, the following. The anion exchange liquid may be diluted with a solvent, such as kerosene, to control the volume and concentration of the ion exchange reagent. To keep the back extraction ion (hydroxyl ion) concentration sufficiently high to drive the entire process, the back extraction liquid (introduced through line 23) should be maintained relatively high, preferably above pH 11.

The CMA slurry exiting line 31 may be recovered as desired, such as by drying, evaporation, crystallization or a combination thereof. The preferred method is to react residual lime (dolime) with additional acetic acid and crystallize the product.

Among the useful anion exchange liquids are in the quaternary amine compounds under the trademark ALIQUAT ® made by Henkel. The broth which is introduced into the extraction tank 17 should be cell-free and may be made so by centrifugation, filtration or other convenient means.

To test the amount of acetate ion exchange as a function of pH, a feed comprising 50 gm/liter vinegar was utilized and extracted with an organic phase comprising 10 vol % ALIQUAT ® 336 in kerosene. The results are shown in the following table.

| Feed pH | Ave. Dist. Ratio D | Minimum Acetate g/l |
|---------|--------------------|--------------------|
| 2.5     | 0.3                | 8                   |
| 4.5     | 0.7                | 3                   |
| 6.0     | 1.2                | 0.3                 |

Feed: 50 g/l vinegar (acetic acid)
Organic: 10 vol % ALIQUAT ® 336 in kerosene

As can be seen from the table, as the pH of the feed material is increased, the distribution ratio between the organic phase and the aqueous phase increases and the amount of acetate remaining in the aqueous phase decreases.

What is claimed is:

1. A method for extracting acetate anion from an aqueous fermentation broth comprising the steps of
   (a) contacting an aqueous acetate containing liquid with a water immiscible extraction liquid comprising a quanternary ammonium exchange reagent which exchanges hydroxide anion with said acetate anion to thereby extract said acetate anion from said fermentation broth into said extraction liquid;
   (b) separating said extraction liquid containing said acetate from said aqueous broth;
   (c) contacting said extraction liquid containing said acetate with a second aqueous phase comprising calcium and magnesium hydroxides or oxides which react with said acetate to form a water soluble product dissolved in said second aqueous phase;
   (d) separating said second aqueous phase containing said dissolved product from said extraction liquid;
   (e) optionally, isolating said product from said second aqueous phase.

2. A method according to claim 1 wherein said broth is substantially cell-free.

3. A method according to claim 1 wherein said water-immiscible extraction liquid further comprises an organic diluent.

4. A method according to claim 3 wherein said diluent comprises kerosene.

5. A method according to claim 1 wherein said calcium and magnesium oxides or hydroxides are in the form of dolomitic lime.

6. A method according to claim 1 wherein said method is performed in a continuous manner and at least a portion of said extraction liquid in said step (d) is recycled for use in said step (c).

7. A method according to claim 3 wherein at least a portion of said aqueous liquid from said step (b) is recycled for use in fermentation to form said aqueous acetate containing liquid.

8. A method according to claim 1 wherein said step (d) comprises evaporation of liquids to produce said solid calcium-magnesium acetate.

9. A method according to claim 1 wherein said step (e) comprises adding acetic acid to said second aqueous phase, to quench residual calcium and magnesium bases, if present, and crystallizing calcium-magnesium acetate from said second aqueous phase.

* * * * *